(12) United States Patent
Lockridge et al.

(10) Patent No.: US 11,532,826 B2
(45) Date of Patent: Dec. 20, 2022

(54) APPARATUS AND METHOD FOR BATTERY PASSIVATION COMPENSATION IN A MEDICAL DEVICE

(71) Applicant: Roche Diabetes Care, Inc., Indianapolis, IN (US)

(72) Inventors: Larry Lewis Lockridge, Fishers, IN (US); Duane Patrick Fridley, Indianapolis, IN (US); Kurt Gerard Klem, Indianapolis, IN (US); Michael Joseph Blackburn, Indianapolis, IN (US); Nathan Eugene Manlove, Noblesville, IN (US); Steven Kent Moore, Carmel, IN (US); Marshall M. Parker, Indianapolis, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 537 days.

(21) Appl. No.: 16/720,273

(22) Filed: Dec. 19, 2019

(65) Prior Publication Data
US 2021/0186384 A1 Jun. 24, 2021

(51) Int. Cl.
*H01M 6/50* (2006.01)
*H02J 7/00* (2006.01)
(Continued)

(52) U.S. Cl.
CPC .......... *H01M 6/50* (2013.01); *A61B 5/14532* (2013.01); *H01M 10/44* (2013.01); *H02J 7/0047* (2013.01);
(Continued)

(58) Field of Classification Search
None
See application file for complete search history.

(56) References Cited

U.S. PATENT DOCUMENTS 4,839,248 A 6/1989 Magnussen, Jr. et al.
6,118,251 A 9/2000 Atwater
(Continued)

OTHER PUBLICATIONS

Spectrum Batteries Inc., "Passivation", available: www.spectrumbatteries.com/id6.html, retrieved Oct. 14, 2019 (2 pages).
(Continued)

*Primary Examiner* — Kennedy Schaetzle (57) ABSTRACT

A method for operating a medical device includes activating a processor in the medical device in a low-power operating mode, measuring a first voltage level of the battery, applying at least one discharge pulse to the battery in response to the first voltage level of the battery being greater than a predetermined passivation minimum voltage threshold and less than a predetermined passivation maximum voltage threshold, measuring a second voltage level of the battery after the at least one discharge pulse, and operating the processor in the medical device in an increased-power operating mode to continue operation of the medical device only in response to the second voltage level being greater than or equal to a predetermined operating voltage threshold, the predetermined operating voltage threshold being greater than the predetermined passivation minimum voltage threshold and less than or equal to the predetermined passivation maximum voltage threshold.

20 Claims, 4 Drawing Sheets

(51) Int. Cl.
*A61B 5/145* (2006.01)
*H01M 10/44* (2006.01)
(52) U.S. Cl.
CPC ...... *H02J 7/0063* (2013.01); *H02J 7/007182* (2020.01); *A61B 2560/0209* (2013.01); *A61B 2560/0214* (2013.01); *A61B 2562/028* (2013.01); *H02J 7/00041* (2020.01)

(56) References Cited

U.S. PATENT DOCUMENTS

| | | | |
|---|---|---|---|
| 7,248,920 B2 | 7/2007 | Norton et al. | |
| 8,847,785 B2 | 9/2014 | Heath | |
| 9,587,321 B2 | 3/2017 | Viavattine et al. | |
| 10,268,229 B2 | 4/2019 | Stever | |
| 2009/0248100 A1* | 10/2009 | Vaisnys | A61N 1/3975 607/5 |
| 2011/0315564 A1 | 12/2011 | Guthrie et al. | |
| 2014/0338181 A1* | 11/2014 | Allgaier | H01M 10/446 29/593 |
| 2015/0270725 A1* | 9/2015 | Sorin | H01M 10/425 320/136 |

OTHER PUBLICATIONS

International Search Report and Written Opinion; PCT/US2020/064433; dated Apr. 22, 2021; pp. 1-10.

* cited by examiner

APPARATUS AND METHOD FOR BATTERY PASSIVATION COMPENSATION IN A MEDICAL DEVICE

TECHNICAL FIELD

The disclosure relates generally to the field of battery powered medical devices and, more specifically, to battery powered medical devices that are susceptible to battery passivation, including blood glucose test meters.

BACKGROUND

Analyte test meters that are known to the art enable the analysis of a bodily fluid sample provided by a user to identify the level of one or more analytes in the body of the user using an electronic device and one or more electrochemical reactions. These analyte meters provide significant benefits for the accurate measurement of analytes in fluidic samples (i.e., biological or environmental) for individual users. An analyte meter applies electrical signals to the combination of the reagents and the fluid sample and records responses to the applied electrical signals, and a combination of electronic hardware and software in the analyte test meter implements a detection engine that detects a level of the analyte in the body of the user based on the recorded responses to the electrical signals. For example, persons with diabetes can benefit from measuring glucose by providing a fluid sample of blood or another bodily fluid to reagents that are formed on an electrochemical test strip, which is electrically connected to a blood glucose meter (BGM). The BGM provides a measurement of the blood glucose level of the user, and many BGM devices use single-use electrochemical test strips that are discarded after each blood glucose measurement. Analyte test meters can also provide benefits to users at-risk for heart disease by providing measurements of cholesterols and triglycerides, among other analytes. These are but a few examples of the benefits of measuring analytes in biological samples. Advancements in the medical sciences are identifying a growing number of analytes that can be electrochemically analyzed in a fluidic sample.

Many existing analyte test meters use batteries as an energy source to power the electronic components of the analyte meters and to provide a compact and portable test meter that a person with diabetes (PwD) or other medical user carries about his or her person. In typical use, the test meter is activated for use over a comparatively short period, often one minute or less for obtaining a blood glucose measurement, during which one or more batteries provide electrical current to operate components in the test meter. The test meter undergoes comparatively prolonged periods in a deactivated or "hibernation" mode in which the test meter is inactive and the batteries in the test meter provide little or no electrical current to the test meter. For example, even in a heavy usage scenario in which a PwD performs ten tests of his or her blood sugar during a day, the blood glucose meter spends the large majority of the day in the deactivated mode, and many blood glucose meters experience lower-frequency usage that produces even longer periods of inactivity. For example, some PwDs test blood sugar only three times per day, and some PwDs who employ continuous glucose monitors (CGMs) only use a portable blood glucose meter on an infrequent basis (e.g. once every few days or even weeks/months) to verify and supplement data from a CGM.

Passivation is one issue that affects existing batteries during prolonged periods of inactivity in which the batteries produce little or no current to drive a load. As a non-limiting example, passivation occurs in non-rechargeable lithium batteries when a passivation layer of lithium chloride forms on a surface of lithium in the anode of the battery. The passivation layer reduces the nominal voltage level of the battery, which mimics the effects of actually discharging the battery to a reduced voltage level, although the passivation process does not substantially discharge the battery and in fact the passivation process may inhibit "self-discharge" of a battery. Passivation occurs over periods of time when the battery does not discharge appreciable amounts of current, and large changes in temperature in the environment around the battery facilitate the passivation process. Since users typically carry blood glucose monitors and other battery-powered medical devices with them through various weather conditions and may leave these devices in vehicles or other locations that experience large hot and cold temperature swings, passivation is a possibility in the batteries used in these devices.

As described above, passivation reduces the nominal voltage level of a battery. In some circumstances, a medical device incorrectly identifies that a battery has been discharged to a point where the battery cannot be used to operate the medical device because the reduction in voltage due to passivation is similar to the reduction in voltage that occurs as the battery discharge. This problem is compounded because in many devices the same battery that may be passivated or discharged is also the sole source of energy to operate the voltage measurement devices and other electronic components that determine if the battery has sufficient charge to enable normal operation of the medical device. Consequently, improvements to blood glucose meters and other battery powered medical devices that detect and compensate for battery passivation would be beneficial.

SUMMARY

In one embodiment, a method for operating a medical device to compensate for battery passivation has been developed. The method includes activating a processor in the medical device in a low-power operating mode, the processing receiving electrical power from a battery electrically connected to the medical device, measuring, with the processor, a first voltage level of the battery, applying, with the processor, at least one discharge pulse to the battery in response to the first voltage level of the battery being greater than a predetermined passivation minimum voltage threshold and less than a predetermined passivation maximum voltage threshold, measuring, with the processor, a second voltage level of the battery after the at least one discharge pulse, and operating the processor in the medical device in an increased-power operating mode to continue operation of the medical device only in response to the second voltage level being greater than or equal to a predetermined operating voltage threshold, the predetermined operating voltage threshold being greater than the predetermined passivation minimum voltage threshold and less than or equal to the predetermined passivation maximum voltage threshold.

In another embodiment, a method for operating a medical device to compensate for battery passivation has been developed. The method includes activating a processor in the medical device in a low-power operating mode, the processing receiving electrical power from a primary battery electrically connected to the medical device, measuring, with the processor, a first voltage level of the primary battery, receiving, with the processor, a second voltage level of a secondary battery electrically connected to the medical device that provides electrical power to at least one peripheral device in the medical device, increasing a clock speed of the processor to apply at least one discharge pulse to the primary battery in response to the first voltage level of the primary battery being greater than a predetermined passivation minimum voltage threshold and less than a predetermined passivation maximum threshold, activating, with the processor, the at least one peripheral device in the medical device to apply at least one discharge pulse to the secondary battery in response to the second voltage level of the secondary battery being greater than the predetermined passivation minimum voltage threshold and less than the predetermined passivation maximum threshold, measuring, with the processor, a third voltage level of the primary battery after the at least one discharge pulse applied to the primary battery, measuring, with the processor, a fourth voltage level of the secondary battery after the at least one discharge pulse applied to the secondary battery, and operating the processor in the medical device in the increased-power operating mode and activating the at least one peripheral to continue operation of the medical device only in response to the third voltage level being greater than or equal to a first predetermined operating voltage threshold, the first predetermined operating voltage threshold being greater than the predetermined passivation minimum voltage threshold and less than or equal to the predetermined passivation maximum voltage threshold, and the fourth voltage level being greater than or equal to a second predetermined operating voltage threshold, the second predetermined operating voltage threshold being greater than the predetermined passivation minimum voltage threshold and less than or equal to the predetermined passivation maximum voltage threshold.

In another embodiment, a medical device that is configured to compensate for battery passivation has been developed. The medical device includes a processor that is configured to be connected to a battery to receive electrical power from the battery. The processor is configured to activate in a low-power operating mode, measure a first voltage level of the battery, apply at least one discharge pulse to the battery in response to the first voltage level of the battery being greater than a predetermined passivation minimum voltage threshold and less than a predetermined passivation maximum voltage threshold, measure a second voltage level of the battery after the at least one discharge pulse, and operate the processor in an increased-power operating mode to continue operation of the medical device only in response to the second voltage level being greater than or equal to a predetermined operating voltage threshold, the predetermined operating voltage threshold being greater than the predetermined passivation minimum voltage threshold and less than or equal to the predetermined passivation maximum voltage threshold.

In another embodiment, a medical device that is configured to compensate for battery passivation has been developed. The medical device includes a processor configured to receive electrical power from a primary battery electrically connected to the medical device, at least one peripheral device in the medical device operatively connected to the processor and configured to receive electrical power from a secondary battery electrically connected to the medical device. The processor is configured to activate in a low-power operating mode, measure a first voltage level of the primary battery, receive a second voltage level of the secondary battery, increase a clock speed of the processor to apply at least one discharge pulse to the primary battery in response to the first voltage level of the primary battery being greater than a predetermined passivation minimum voltage threshold and less than a predetermined passivation maximum threshold, activate the at least one peripheral device in the medical device to apply at least one discharge pulse to the secondary battery in response to the second voltage level of the secondary battery being greater than the predetermined passivation minimum voltage threshold and less than the predetermined passivation maximum threshold, measure a third voltage level of the primary battery after the at least one discharge pulse applied to the primary battery, measure a fourth voltage level of the secondary battery after the at least one discharge pulse applied to the secondary battery, and operate the processor in the medical device in the increased-power operating mode and activating the at least one peripheral to continue operation of the medical device only in response to the third voltage level being greater than or equal to a first predetermined operating voltage threshold, the first predetermined operating voltage threshold being greater than the predetermined passivation minimum voltage threshold and less than or equal to the predetermined passivation maximum voltage threshold, and the fourth voltage level being greater than or equal to a second predetermined operating voltage threshold, the second predetermined operating voltage threshold being greater than the predetermined passivation minimum voltage threshold and less than or equal to the predetermined passivation maximum voltage threshold.

BRIEF DESCRIPTION OF THE DRAWINGS

The advantages, effects, features and objects other than those set forth above will become more readily apparent when consideration is given to the detailed description below. Such detailed description makes reference to the following drawings, wherein.

DETAILED DESCRIPTION

These and other advantages, effects, features and objects are better understood from the following description. In the description, reference is made to the accompanying drawings, which form a part hereof and in which there is shown by way of illustration, not limitation, embodiments of the inventive concept. Corresponding reference numbers indicate corresponding parts throughout the several views of the drawings.

While the inventive concept is susceptible to various modifications and alternative forms, exemplary embodiments thereof are shown by way of example in the drawings and are herein described in detail. It should be understood, however, that the description of exemplary embodiments that follows is not intended to limit the inventive concept to the particular forms disclosed, but on the contrary, the intention is to cover all advantages, effects, and features falling within the spirit and scope thereof as defined by the embodiments described herein and the claims below. Reference should therefore be made to the embodiments described herein and claims below for interpreting the scope of the inventive concept. As such, it should be noted that the embodiments described herein may have advantages, effects, and features useful in solving other problems.

The devices, systems and methods now will be described more fully hereinafter with reference to the accompanying drawings, in which some, but not all embodiments of the inventive concept are shown. Indeed, the devices, systems and methods may be embodied in many different forms and should not be construed as limited to the embodiments set forth herein; rather, these embodiments are provided so that this disclosure will satisfy applicable legal requirements.

Likewise, many modifications and other embodiments of the devices, systems and methods described herein will come to mind to one of skill in the art to which the disclosure pertains having the benefit of the teachings presented in the foregoing descriptions and the associated drawings. Therefore, it is to be understood that the devices, systems and methods are not to be limited to the specific embodiments disclosed and that modifications and other embodiments are intended to be included within the scope of the claims. Although specific terms are employed herein, they are used in a generic and descriptive sense only and not for purposes of limitation.

Unless defined otherwise, all technical and scientific terms used herein have the same meaning as commonly understood by one of skill in the art to which the disclosure pertains. Although any methods and materials similar to or equivalent to those described herein can be used in the practice or testing of the methods, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one." Likewise, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. For example, the expressions "A has B," "A comprises B" and "A includes B" may refer both to a situation in which, besides B, no other element is present in A (i.e., a situation in which A solely and exclusively consists of B) or to a situation in which, besides B, one or more further elements are present in A, such as element C, elements C and D, or even further elements.

Figure 1:
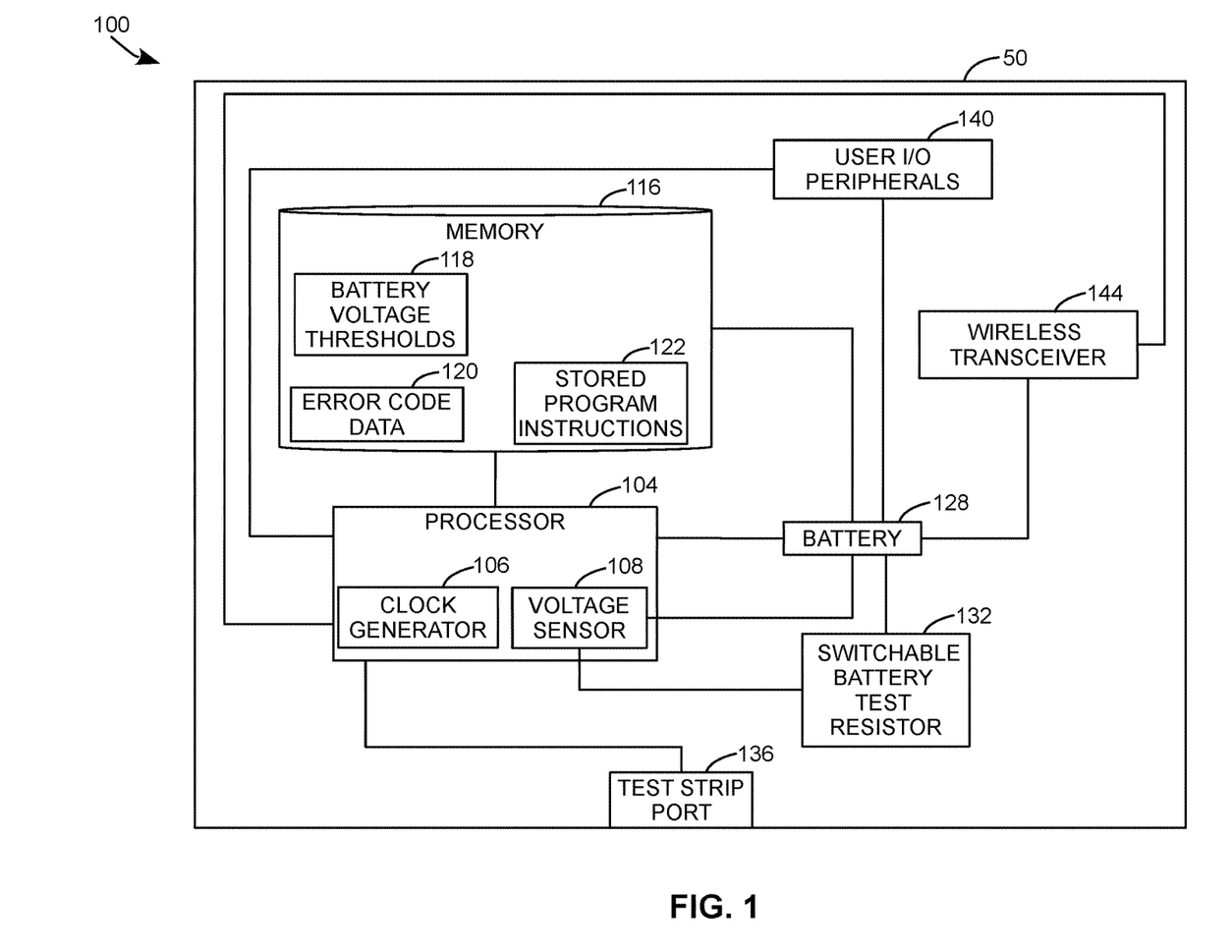
FIG. 1 is a schematic diagram of a battery-powered medical device, which is further depicted as a blood glucose monitor that operates using a single battery.

FIG. 1 depicts a schematic diagram of a battery-powered medical device 100 that is configured to compensate for battery passivation. A housing 50 in the medical device 100 includes a receptacle for a replaceable battery 128 that is electrically connected to the medical device 100 and houses the other components of the medical device 100. The medical device 100 operates using electrical power delivered from the battery 128 to operate a processor 104 memory 116, user input/output (I/O) peripherals 140, and a wireless transceiver 144 peripheral device. In the illustrative embodiment of FIG. 1, the battery 128 is a single lithium battery that is available commercially as a CR2032 coin cell battery with a nominal 3 V voltage level in a fully-charged battery. However, in alternative embodiments the battery 128 is a different type of battery that can experience passivation. Furthermore, in alternative embodiments what is referred to as the single battery 128 further includes multiple battery cells that are electrically connected in a series, a parallel, or a series-parallel configuration to act as a power source for components in a medical device. In the illustrative example of FIG. 1, the medical device 100 is a blood glucose meter that includes a test strip port 136. The test strip port 136 receives a portion of an electrochemical test strip and provides electrical connections between electrodes in the test strip and the processor 104 to enable the processor 104 to apply signals in an electrical test sequence and receive response signals from the test strip to enable measurement of glucose levels in a blood sample that is applied to the test strip 136. Other medical device embodiments that do not perform blood glucose measurements or other forms of electrochemical analyte measurement do not include the test strip port 136.

In the medical device 100, the processor 104 includes one or more digital logic devices such as a microcontroller, microprocessor, application specific integrated circuit (ASIC), or any other electronic device or devices that implement the digital logic functions to perform the operations for battery passivation compensation and for operation of the medical device 100. While not depicted in further detail herein, the processor 104 also incorporates or is operatively connected to digital-to-analog converters, drive signal generators, signal measurement circuits, and analog-to-digital converters and any other electronic components that are required for the processor 104 to generate an electrical test sequence that is applied to electrodes in an electrochemical test strip through the test strip port 136 and for the processor 104 to detect electrical response signals from the electrochemical test strip in response to the electrical test sequence. While not depicted in greater detail, the processor 104 also includes input/output (I/O) hardware that operatively connects the processor 104 to the I/O peripherals 140, the wireless transceiver 144, and the memory 116.

In the medical device 100, the processor 104 incorporates or is operatively connected to a clock generator 106. The clock generator 106 includes an oscillator and other electronic components that are generally known to the art to generate a clock signal that synchronizes the execution of operations of the processor 104. The clock generator 106 generates clock signals with at least two different frequencies that adjusts the speed of execution of instructions in the processor 104, which in turn affects the level of electrical power consumption of the processor 104 during operation with lower-frequency clock speeds drawing lower power levels than higher-frequency clock speeds. In one configuration, the processor 104 operates in a low-power operating mode with the clock generator 106 producing a 1 MHz clock signal and the processor 104 operates in an increased-power operating mode with the clock generator 106 producing a 16 MHz clock signal. Of course, alternative processor configurations employ clock generators that produce different specific clock frequencies and clock generators are configurable to generate clock signals at three or more different frequencies as well.

In the medical device 100, the processor 104 incorporates or is operatively connected to a voltage sensor 108, which includes an analog voltage measurement device and an analog-to-digital converter that provides digital data corresponding to the voltage of the battery 128 to the processor 104. The voltage sensor 108 is operatively connected to the battery 128 and to a switchable battery test resistor 132. The voltage sensor 108 detects a voltage across the terminals of the battery 128 both when the battery 128 is minimally loaded and when the battery 128 is connected to the switchable battery test resistor 132. The switchable battery test resistor 132 includes a resistor with a predetermined resistance level (e.g. 8200) that applies a high-impedance load across the terminals of the battery 128. The high-impedance load draws minimal current from the battery 128, but enables the voltage sensor 108 to measure both an open-circuit and loaded voltage level of the battery 128. The processor 104 operates a switch, such as a solid-state switching transistor or relay, to connect the resistor to the battery 128 to enable the voltage sensor 108 to measure the voltage of the battery 128 while under a predetermined load and to disconnect the battery test resistor 132 from the battery 128 after measuring the voltage.

In the medical device 100, the memory 116 is a digital data storage device that includes at least one non-volatile data storage device such as an EEPROM, NAND or NOR flash, phase change memory, or other suitable data storage devices that retain stored digital data in the absence of electrical power from the battery 128. The memory 116 further includes one or more volatile memory devices including a static or dynamic random-access memory (RAM) that is either integrated into the processor 104 or is embodied as a separate memory device. The memory 116 holds a set of battery voltage thresholds 118, recorded error code data 120, and stored program instructions 122 that the processor 104 executes to perform the battery passivation compensation operations and other functions of a medical device that are described herein.

The battery voltage thresholds 118 include predetermined data indicating the levels of battery voltage that are sufficient to enable operation of the medical device 100 without regard to potential battery passivation (high battery voltage threshold), a minimum operating voltage level that enables operation of the medical device where the medical device 100 potentially needs to compensate for battery passivation to reach the operating voltage (operating voltage threshold), and a minimum voltage level at or beneath which the medical device 100 will not continue operation even if the battery 128 is affected by passivation (minimum voltage threshold). Table 1 depicts an illustrative example of voltage thresholds in a blood glucose meter that operates using a lithium battery 128 with a 3 V nominal voltage level, although the precise voltage thresholds may vary based on the battery configuration and voltage requirements of electronic components in different medical devices:

TABLE 1

| Voltage thresholds for single battery | |
|---|---|
| Passivation Maximum Voltage Threshold | 2.60 V |
| Passivation Minimum Voltage Threshold | 1.80 V |
| High Battery Voltage Threshold | 2.50 V |
| Operating voltage threshold [minimum] | 2.46 V |
| Minimum Voltage Threshold | 2.40 V |

In Table 1, the passivation maximum voltage threshold corresponds to the maximum voltage at which the medical device 100 attempts to perform a passivation compensation process to reduce or eliminate passivation in a battery, and if the battery voltage exceeds this threshold then passivation compensation is not necessary for standard operation of the medical device 100. The passivation minimum voltage threshold corresponds to the minimum voltage level in the battery that is required for the medical device 100 to compensate for potential passivation. If the voltage level of the battery is less than the passivation minimum voltage threshold, then the medical device 100 deactivates without attempting to compensate for battery passivation.

The high battery voltage threshold, the operating voltage threshold, and the minimum voltage threshold refer to battery voltage levels that affect the operation of the medical device 100 after completing a passivation compensation operation. The high battery voltage threshold indicates a voltage at or above which the medical device 100 can perform standard operations without any further testing of the battery 128. The high battery voltage threshold is generally set below the nominal voltage level of a fully charged battery (3 V in the example of the medical device 100). The operating voltage threshold represents the minimum voltage level at which the medical device 100 can continue operation, although the medical device 100 optionally generates an output informing the user that the level of charge of the battery is approaching the point of requiring battery replacement. For example, in one embodiment the processor 104 generates an output via, for example, a display device or indicator light that the battery 128 should be replaced soon if the voltage level is greater than or equal to the predetermined operating voltage threshold but below the predetermined high battery voltage threshold. However, the medical device 100 continues operation if the battery voltage is greater than or equal to the predetermined operating voltage threshold. The voltage range above the minimum voltage threshold and below the operating voltage threshold indicates voltage levels where the medical device 100 cannot complete standard operations without an unacceptable risk of malfunction due to the low battery voltage, but in this voltage range the processor 104 remains operable to generate an error message output that alerts the user to the need to replace the battery 128. The minimum voltage threshold indicates a level at which the medical device cannot continue operation even to emit battery error messages without an unacceptable risk of a malfunction, and beneath this threshold the processor 104 performs a device shutdown operation without attempting to compensate for potential battery compensation. Those of skill in the art will note that the minimum voltage threshold is not indicative of a completely discharged battery since the battery 128 still retains some charge that is sufficient to at least enable minimal operation of the processor 104 to test battery voltage. As is generally known in the art, a severely discharged or absent battery will prevent activation of the processor 104 in the first instance.

The embodiments described herein enable the medical device 100 to compensate for battery passivation that reduces the voltage of the battery 128 in the voltage ranges between the passivation maximum voltage threshold and the passivation minimum voltage threshold. In the event that the battery 128 has experienced passivation, the compensation processes described herein can increase the voltage of the battery 128 above the operating voltage threshold or the high battery threshold in at least some circumstances. The passivation compensation reduces or eliminates false error messages indicating the need to replace the battery 128 or a premature failure of the medical device 100 to operate with the battery 128. While the example depicted above includes a passivation high voltage threshold that is greater than the high battery voltage threshold and a passivation minimum voltage threshold that is less than the minimum voltage threshold, in an another configuration a least one of the passivation high voltage threshold is equal to the high battery voltage threshold and the passivation minimum voltage threshold is equal to the minimum voltage threshold. Furthermore, in some embodiments the operating voltage threshold has the same voltage level as the high battery voltage threshold, the passivation maximum voltage threshold, or both of these thresholds instead of being less than the high battery voltage threshold and the passivation maximum voltage threshold as depicted in Table 1.

Referring again to FIG. 1, the user I/O peripherals 140 include input devices and output devices that enable user interaction with the medical device 100. Examples of input devices include touchpads and touchscreen inputs, buttons, switches, dials, and the like. At least some types of input devices receive electrical power from the battery 128, either directly or via drive circuitry in the processor 104. The output devices include display devices such as LCD or OLED display screens, indicator lights, audio output speakers, electromechanical actuators for haptic feedback devices, and the like, and these output devices also draw electrical power from the battery 128 directly or via drive circuitry in the processor 104.

The wireless transceiver 144 is, for example, a Bluetooth, Bluetooth Low Energy (BLE), IEEE 802.11 "Wi-Fi", Near Field Communication (NFC), cellular, or other wireless transceiver that enables the medical device 100 to perform wireless communication with external computing devices including, but not limited to, smartphones, personal computers (PCs), and network services via a data network. In one non-limiting embodiment, the wireless transceiver 144 is implemented as a BLE transceiver with an antenna that contained within the housing 50. The wireless transceiver 144 receives electrical power from the battery 128 either directly or via drive circuitry in the processor 104. In some medical device embodiments, the wireless transceiver 144 draws a substantial level of power from the battery 128 during operation, and in particular during radio transmission operations. The wireless transceiver 144 is an optional component that need not be included in every embodiment of a medical device since some medical devices are not configured for wireless communication with external computing devices.

Figure 2:
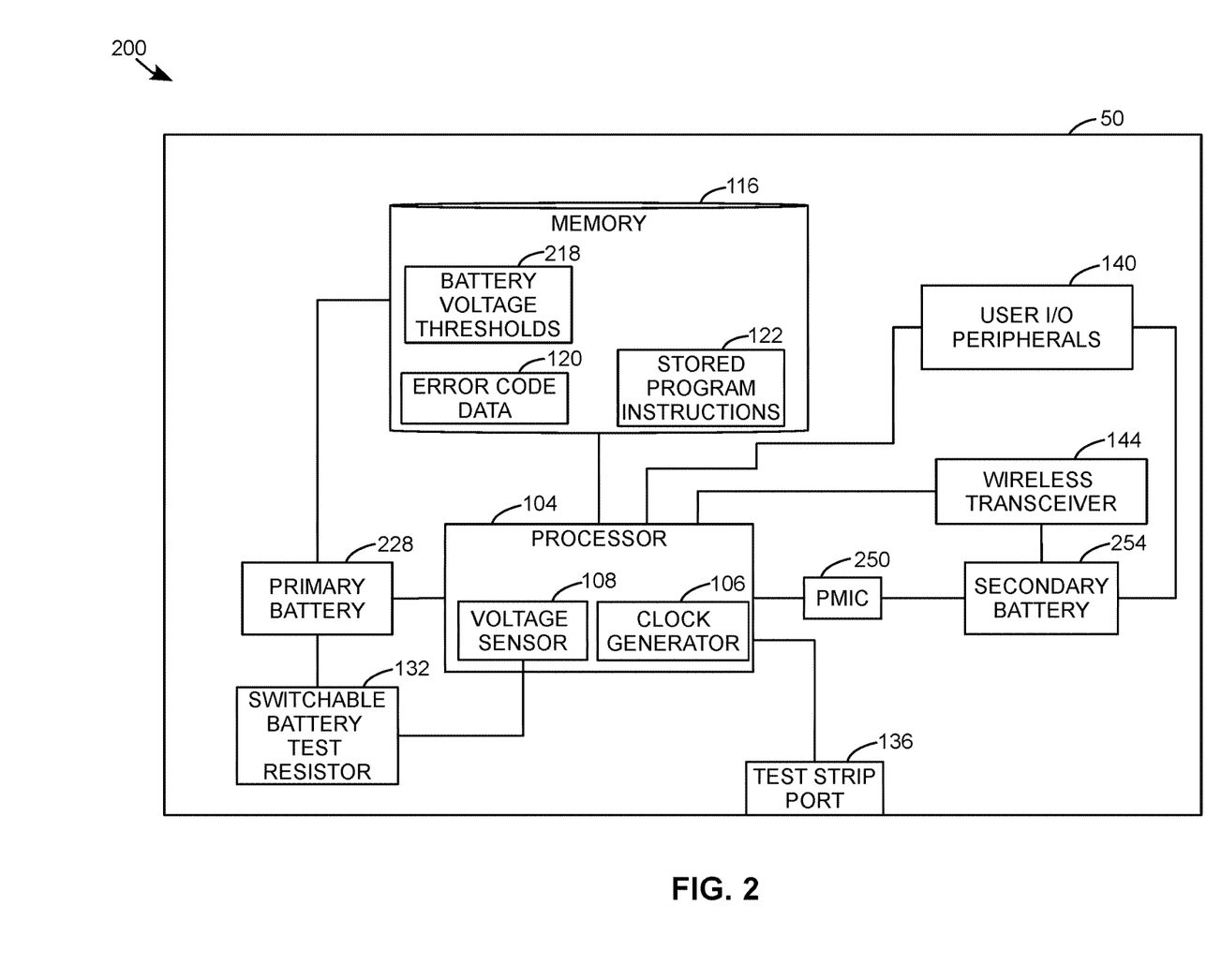
FIG. 2 is a schematic diagram of a battery-powered medical device, which is further depicted as a blood glucose monitor that operates using two batteries.

FIG. 2 depicts a schematic diagram of another battery-powered medical device 200. The medical device 200 includes some common elements to the medical device 100 including a housing 50, processor 104, memory 116, user I/O peripherals 140, and wireless transceiver 144. The medical device 200 is also depicted as a blood glucose meter that includes a test strip port 136. Unlike the medical device 100, the medical device 200 includes receptacles for two different replaceable batteries, which are depicted as a primary battery 228 and a secondary battery 254 that are both electrically connected to the medical device 200. In the configuration of FIG. 2, the primary battery 228 provides electrical power to the processor 104, including components that generate electrical test signals for the test strip port 136, and the memory 116. The secondary battery 254 provides electrical power to drive the wireless transceiver 144 and the user I/O peripherals 140. In the medical device 200, the processor 104 uses the voltage sensor 108 and switchable battery test resistor 132 to measure the voltage level of the primary battery 228 in a similar manner to that described above in FIG. 1, while a separate power management integrated circuit (PMIC) 250 provides voltage measurements of the secondary battery 254 to the processor 104. In the illustrative example of FIG. 2, both the primary battery 228 and the secondary battery 254 are lithium batteries that are available commercially as a CR2032 coin cell batteries with a nominal 3 V voltage level in a fully-charged battery.

In the embodiment of FIG. 2, either or both of the primary battery 228 and the secondary battery 254 may experience passivation, and the two batteries may generate different voltage levels during the course of operation of the medical device 200. The memory 116 stores battery voltage thresholds 218 that are similar to the battery thresholds 118 in the medical device 100, but optionally include separate sets of voltage threshold values for the primary battery 228 and the secondary battery 254, although in some embodiments both the primary battery 228 and the secondary battery 254 use the same voltage threshold values. Table 2 depicts an illustrative example of voltage thresholds in a blood glucose meter that operates using two lithium batteries with 3 V nominal voltage levels, although the precise voltage thresholds may vary based on the battery configuration and voltage requirements of electronic components in different medical devices:

TABLE 2

| Voltage thresholds for primary and secondary battery | |
|---|---|
| Passivation Maximum Voltage Threshold [primary and secondary] | 2.60 V |
| Passivation Minimum Voltage Threshold [primary and secondary] | 1.80 V |
| Primary High Battery Voltage Threshold | 2.50 V |
| Primary Operating voltage threshold [minimum] | 2.46 V |
| Primary Minimum Voltage Threshold | 2.40 V |
| Secondary High Battery Voltage Threshold | 2.42 V |
| Secondary Operating voltage threshold [minimum] | 2.35 V |
| Secondary Minimum Voltage Threshold | 2.30 V |

In the embodiment of FIG. 2, the processor 104 in the medical device 200 uses the same passivation maximum voltage threshold and passivation minimum voltage threshold values for both the primary battery 128/228 and the secondary battery 254, although an alternative configuration may employ different passivation maximum and minimum voltage thresholds for the primary and secondary batteries. The processor 104 uses the primary high battery voltage threshold, primary operating voltage threshold, and primary minimum voltage threshold in substantially the same manner described above for the corresponding voltage thresholds in the medical device 100. The secondary high battery voltage threshold, secondary operating voltage threshold, and secondary minimum voltage threshold have a similar function to the corresponding thresholds described above as the processor 104 compensates for potential passivation in the secondary battery 254 to enable operation of the wireless transceiver 144 using electrical power from the secondary battery 254. Additional details of the operation the medical devices 100 and 200 are provided below with reference to the processes of FIG. 3 and FIG. 4.

Figure 3:
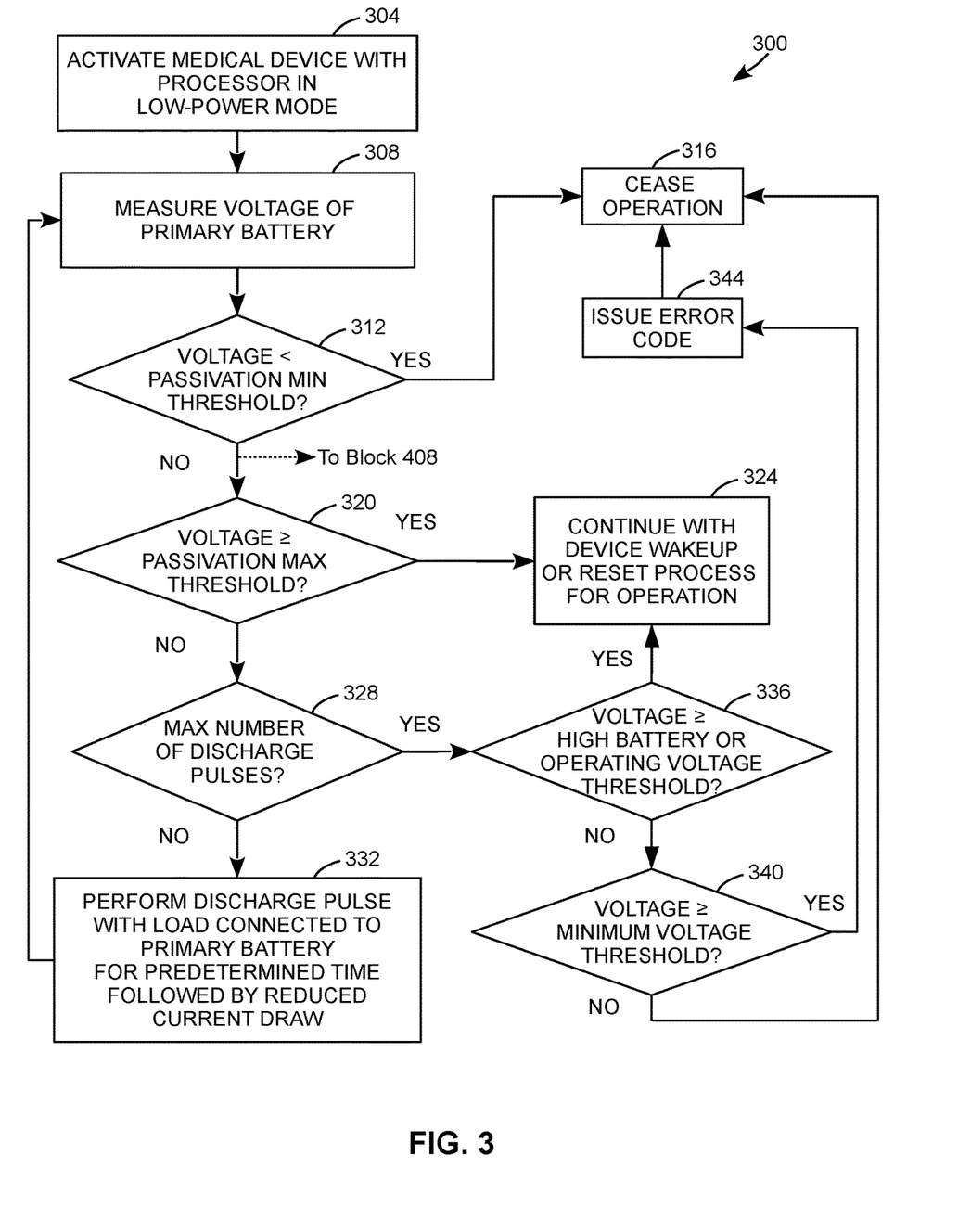
FIG. 3 is a block diagram of a process for detecting and compensating for passivation in the battery of a battery-powered medical device including the battery of the blood glucose meter of FIG. 1 and the primary battery of the blood glucose meter of FIG. 2.

FIG. 3 depicts a block diagram of a process 300 for activating a battery-powered medical device to compensate for passivation in a battery in the medical device. In particular, the process 300 is applicable to the medical device 100 using a single battery 128 and to the primary battery 228 in the medical device 200. These batteries are referred to interchangeably in the context of the process 300 unless otherwise noted herein. In the description below, a reference to the process 300 performing a function or action refers to the operation of a processor to execute stored program instructions to perform the function or action in association with other components of a medical device.

The process 300 begins with activation of the processor 104 in a low-power operating mode (block 304). In the embodiments of FIG. 1 and FIG. 2, the processor 104 activates in response to insertion of an electrochemical test strip into the test strip port 136 or through a power button, switch, or other input device in the I/O devices 140. As described above, in the low-power operating mode the clock generator 106 produces a reduced frequency clock signal (e.g. 1 MHz) to enable operation of the processor 104 during startup of the medical device at a lower performance level but with a correspondingly reduced power consumption level that enables further battery voltage measurements and compensation for passivation of the battery 128/228.

The process 300 continues as the processor 104 measures the voltage of the battery 128/228 (block 308). In the meters 100 and 200, the processor 104 initially uses a voltage comparator to identify an approximate level of voltage in the battery 128/228 upon startup. If the approximate voltage level of the battery 128/228 is at or above the passivation minimum voltage threshold, then the processor 104 uses the voltage sensor 108 to measure the voltage across the terminals of the battery 128/228 both in an in open-circuit configuration and with the switchable battery test resistor 132 connected to the battery 128/228 to provide a predetermined load. The processor 104 then determines if the measured battery voltage is less than or equal to the passivation minimum voltage threshold that is stored in the memory 116 (block 312) then the processor 104 deactivates itself and any other activated component to cease operation of the medical device 100/200 (block 316). As described above, a battery voltage that is less than or equal to the passivation minimum voltage threshold for the battery 128/228 does not enable stable operation of the medical device 100/200 and the processor 104 performs the shutdown operation to prevent a reset loop or other unstable operations. As described above, if the measured voltage is less than the predetermined passivation minimum voltage threshold then even if battery passivation has occurred, the potential increase in voltage from compensation for the passivation will be unlikely to return the battery to the minimum operating voltage threshold and the passivation compensation process may destabilize operation of the medical device.

During the process 300, if the measured voltage level is greater than the predetermined passivation minimum voltage threshold (block 312) and additionally greater than or equal to the predetermined passivation maximum voltage threshold that is stored in the memory 116 (block 320), then the processor 104 continues with a standard wake from hibernate or device reset operation to begin standard operation of the medical device 100/200 (block 324). For voltage levels that are greater than or equal to the passivation maximum voltage threshold, the battery 128/228 has either not experienced passivation or the effects from passivation can be ignored since the voltage level of the battery is sufficient for normal operation of the medical device. In the embodiments of FIG. 1 and FIG. 2, the wakeup from hibernation process occurs after the medical device 100/200 has completed a successful previous operation, enters a low-power hibernation state, and then returns to operation from hibernation using the same battery 128/228 during the prior operation. The reset process occurs during the first activation of the medical device 100/200 after the battery 128/228 has been replaced, which entails additional processing steps performed by the processor 104 to restore the medical device 100/200 to operation. In both cases, the clock generator 106 increases the clock frequency to operate the processor 104 in the increased power operating mode and the processor 104 operates the memory 116, the user I/O peripherals 140, and the wireless transceiver 144 as needed to operate the medical device 100/200 using power received from the battery 128/228. In the specific configurations of FIG. 1 and FIG. 2, the processor 104 in the blood glucose meter medical device 100/200 operates in the increased-power operating mode to continue operation of the medical device to generate a blood glucose measurement by generating a sequence of electrical test signals that are applied to an electrochemical test strip via the test strip port 136, and the processor 104 measures and generates an output corresponding to the level of glucose in a blood sample on the test strip.

As described above, during the process 300 the processor 104 does not directly compensate for battery passivation in situations where the measured battery voltage is either less than or equal to the predetermined passivation minimum voltage threshold or greater than or equal to the predetermined passivation maximum voltage threshold. However, if the measured battery voltage is both greater than the predetermined passivation minimum battery voltage threshold (block 312) and less than the predetermined passivation maximum voltage threshold (block 320), then the processor 104 controls the application of at least one discharge pulse to the battery 128/228 to compensate for potential passivation in the battery.

A discharge pulse refers to the connection of a load to the battery 128/228 that draws current from the battery for a predetermined time to produce a breakdown in the passivation layer within the battery. The load used for a discharge pulse typically draws a large amount of current from the battery 128/228, which produces changes in the internal of chemistry of the battery that reduces or eliminates the passivation layer and results in an increase in the voltage level of the battery 128/228. After the predetermined time, the processor 104 completes the discharge pulse by waiting for another predetermined idle period time to enable the battery 128/228 to return to a quiescent state, and the processor 104 subsequently performs another voltage measurement to identify the voltage level of the battery 128/228 after the application of the discharge pulse. If the battery 128/228 has experienced passivation, then the voltage of the battery 128/228 after the discharge pulse is greater than the voltage of the battery 128/228 prior to the discharge pulse. In the specific configuration of the medical device 100/200, the processor 104 applies multiple discharge pulses to enable compensation for both larger and smaller levels of battery passivation. If the battery 128/228 has experienced passivation, then the discharge pulses compensate for the passivation and return the battery 128/228 to a higher voltage level that enables operation of the medical device 100/200. Specific examples of discharge pulses in the medical device 100/200 are described in further detail below.

In one configuration, the processor 104 applies the discharge pulse to the battery 128/228 directly as the clock generator 106 increases frequency and the processor 104 operates in the increased-power operating mode at a high clock frequency (e.g. 16 MHz). During the discharge pulse, the processor 104 optionally performs a busy loop or other operations that increase the current draw of the processor 104 but that are not otherwise required to perform the standard operation of the medical device 100/200. In the non-limiting embodiments described herein, the processor 104 operates in the increased-power operating mode at the high frequency clock speed for 300 milliseconds, at which time the clock generator 106 reduces the clock frequency to return the processor 104 to the low-power operating mode for an idle period of 2 milliseconds after which the voltage sensor 108 generates another voltage measurement of the battery 128/228. Of course, alternative embodiments can use different active and idle time periods during a discharge pulse.

In the embodiment of the medical device 100 of FIG. 1, the processor 104 optionally applies the discharge pulse to the battery 128 indirectly by activating a peripheral device that draws current from the battery 128 for a predetermined time. For example, in one configuration the processor 104 activates the wireless transceiver 144 to draw electrical current from the battery 128. The wireless transceiver 144 draws electrical current from the battery 128 for a predetermined period of time (e.g. 300 milliseconds or another predetermined time period) after which the processor 104 deactivates the wireless transceiver and waits for a predetermined idle time period before measuring the voltage level of the battery 128. During the discharge pulse, the wireless transceiver 144 optionally transmits a beacon signal or similar signal that draws electrical current from the battery 128 but that is not part of transmitting medical data during the normal operation of the medical device 100. In another configuration, the processor 104 activates a display device or other user I/O peripheral device 140 that draws sufficient current from the battery 128 to perform the discharge pulse operation. Furthermore, the processor 104 optionally activates multiple peripheral devices such as both the wireless transceiver 144 and a display device or other user I/O peripheral 140 to enable multiple peripherals to draw current from the battery 128. As described in further detail below in FIG. 4, in the medical device 200 that includes the primary battery 228 and the secondary battery 254, a peripheral device is used to apply discharge pulses to the secondary battery 228 since the processor 104 does not draw substantial electrical power from the secondary battery 228. Of course, those of skill in the art will further recognize that the discharge pulse can be applied using a combination of the processor 104, I/O devices 140, and wireless transceiver 144 including applying a discharge pulse by operating the processor 104 at the high frequency clock speed while simultaneously activating the wireless transceiver 144, one or more of the I/O devices 140, or operating all of these components simultaneously.

Referring again to FIG. 3, as described above the processor 104 identifies if the maximum number of discharge pulses have been applied to the battery 128/228 (block 328) and if the maximum number has not been reached, then the processor 104 applies the discharge pulse as described above (block 332). The processor 104 then performs another voltage measurement (block 308) and the process 300 continues in a loop as described above with reference to the processing of blocks 308-332 until either the measured voltage drops to be less than or equal to the predetermined passivation minimum voltage threshold (blocks 312 and 316), the measured voltage rises above the predetermined passivation maximum voltage threshold (blocks 320 and 324), or the measured voltage remains between these thresholds after performing the maximum number of discharge pulses (block 328). In one embodiment of the medical device 100/200, the processor 104 applies a maximum of two discharge pulses, although alternative configurations use one discharge pulse or more than two discharge pulses.

After reaching the maximum number of discharge pulses, the processor 104 identifies if the most recently measured voltage level is greater than or equal to the predetermined high battery voltage level or the predetermined operating voltage threshold (block 336). If the voltage level of the battery 128/228 is greater than or equal to the predetermined high battery voltage threshold or the predetermined operating voltage threshold, then the medical device 100/200 continues with device wakeup or reset process for operation (block 324). In some configurations, during the additional operation that occurs when the voltage level of the battery 128/228 is sufficient for operation (≥predetermined operating voltage threshold) but less than the predetermined high battery voltage threshold, the processor 104 generates a low battery indicator message using one or more of the output peripherals 140 as part of continuing with the device wakeup or reset process. The low battery indicator message is, for example, a graphical icon, indicator light, or audible alarm that alerts the user to the need to a low charge level of the battery and the need replace the battery 128/228 in the near future, although the medical device 100/200 continues operation with the present battery voltage level. As described above, in the embodiments of the medical devices 100 and 200, the processor 104 operates in the increased-power operating mode using the increased clock frequency from the clock generator 106 to continue operation with the other components of the medical device to generate a blood glucose measurement.

During the process 300, if the most recently measured voltage level after reaching the maximum number of discharge pulses is less than the predetermined operating voltage threshold (block 336), then the processor 104 further determines if the measured voltage level of the battery 128/228 is less than the predetermined minimum voltage threshold (bock 340). If the measured voltage level is greater than or equal to the predetermined minimum voltage threshold, then the processor 104 issues an error code related to the battery 128/228 (block 344) and the medical device 100/200 ceases standard operation (block 316). In the configuration of FIG. 1 and FIG. 2, the processor 104 stores an error code with the error code data 120 in a non-volatile portion of the memory 116. In this operating mode, the processor 104 optionally enters a hibernation state in which a display device or other output peripheral 140 produces an output indicating that the battery 128/228 cannot provide sufficient power to enable standard operation of the medical device 100/200 and that replacement is required prior to continued operation. This operating mode provides an opportunity for the medical device 100 to alert the user to the need for battery replacement while the battery 128/228 voltage level remains above the predetermined minimum voltage threshold. During a subsequent startup process with a replacement battery, the processor 104 uses the stored error code data 120 to identify the need to enter the reset operational mode to resume operation using a new battery that has sufficient voltage to enable standard operation of the medical device 100/200. If, however, the measured voltage level remains below the predetermined minimum voltage threshold (block 340) then the processor 104 immediately ceases operation of the medical device 100/200 (block 316) because the battery 128/228 lacks sufficient charge to enable continued operation of the processor 104 in a reliable manner.

As described above, the process 300 enables the medical device 100/200 to apply discharge pulses that compensate for potential battery passivation in the battery 128/228 while using the same battery for operation of the medical device 100/200 during a device startup operation. The passivation compensation process enables the medical device 100/200 to reduce or eliminate false alarm conditions in which the medical device 100/200 incorrectly alerts a user to a low battery condition (when the passivation compensation returns battery voltage to ≥predetermined high battery voltage threshold), to prevent an incorrect battery replacement error that prevents standard operation of the medical device 100/200 (when the passivation compensation returns battery voltage to 2 predetermined operating voltage threshold), or to at least enable the medical device 100/200 to generate an error code and display an error message to alert the user of the need to replace the battery (when the passivation compensation returns battery voltage to 2 predetermined minimum voltage threshold).

Figure 4:
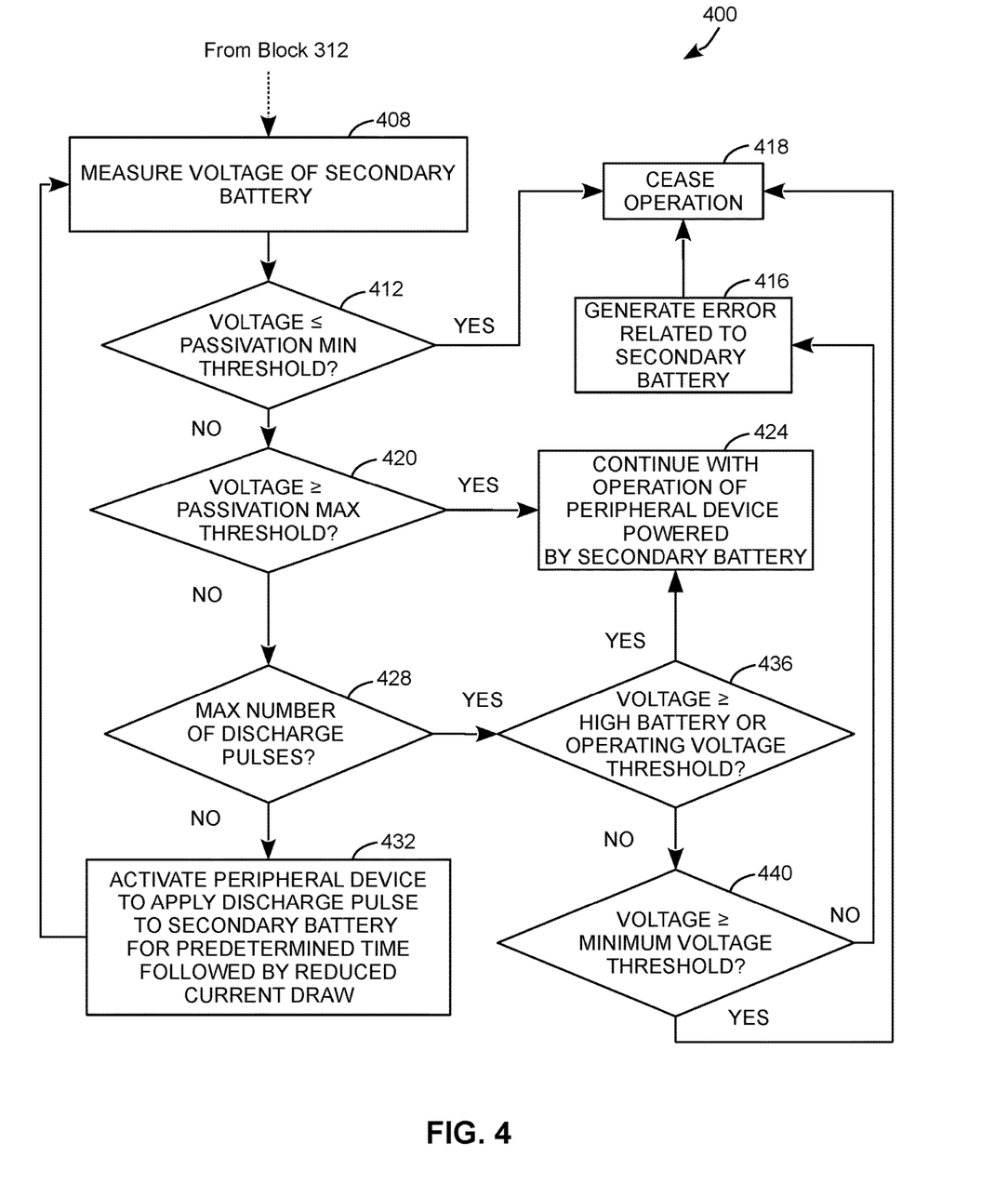
FIG. 4 is a block diagram of a process for detecting and compensating for passivation in a secondary battery of a battery-powered medical device including the secondary battery of the blood glucose meter of FIG. 2.

FIG. 4 depicts a block diagram of a process 400 to compensate for passivation in a secondary battery in a medical device. In particular, the processor 104 in the medical device 200 performs the process 400 to compensate for passivation in the secondary battery 254 in conjunction with performing the process 300 to compensate for passivation in the primary battery 228. In the description below, a reference to the process 400 performing a function or action refers to the operation of a processor to execute stored program instructions to perform the function or action in association with other components of a medical device.

The process 400 begins as the processor 104 receives a voltage measurement for the secondary battery 228 (block 408). In the embodiment of FIG. 2, the PMIC 250 measures the voltage level of the secondary battery 228 and provides a digital representation of the voltage level to the processor 104, although in an alternative embodiment the processor 104 uses a voltage sensor to measure the voltage of the secondary battery 228 directly. As indicated in FIG. 4, the illustrative embodiment of the process 400 starts after the process 300 has begun and the processor 104 has identified that the voltage of the primary battery 228 is at least greater than the predetermined passivation minimum voltage threshold in block 312, which enables the processes 300 and 400 to be performed concurrently. In particular, the processes 300 and 400 enable as least some of the discharge pulses to occur concurrently in some medical devices that perform the process 300 and 400. In an another configuration, the processor 104 performs the process 400 after the process 300 has reached the continued operation state of block 324, where the process 400 is part of the continued wake from hibernation or reset process in the medical device 200.

The process 400 continues as the processor 104 identifies if the measured voltage level of the secondary battery 254 is less than or equal to the predetermined passivation minimum voltage threshold (block 412), and if the voltage level is less than the predetermined passivation minimum voltage threshold then the processor 104 ceases operation of the medical device 200 (block 418). As noted above in Table 2, the predetermined passivation minimum voltage threshold stored in the memory 116 that is associated with the secondary battery 254 may be different than the corresponding passivation minimum voltage threshold of the primary battery 228, and of course the two batteries 228 and 254 may exhibit different voltage levels during operation of the medical device 200.

During the process 400, if the measured voltage of the secondary battery 254 is greater than the predetermined passivation minimum voltage threshold and greater than or equal to the predetermined passivation maximum voltage threshold (block 420) then the processor 104 continues operation of the medical device 200 with standard activation and use of the peripheral device or devices that receive power from the secondary battery 254 (block 424). For example, in the medical device 200 the processor 104 activates the peripheral devices 140 and operates the wireless transceiver 144 as normal during operation to transmit and receive data with external computing devices because the voltage level of the secondary battery 254 is greater than the predetermined passivation maximum voltage threshold for the secondary battery 254. Similarly to the primary battery 228, the processor 104 does not compensate for potential passivation in the secondary battery 254 if the measured voltage level of the secondary battery 254 is either less than or equal to the predetermined minimum voltage threshold or greater than or equal to the predetermined high battery voltage threshold. In the medical device 200, the activation of the peripherals and other operations that occur in response to the secondary batter 254 having sufficient charge are also contingent upon the completion of process 300 to continue with a wakeup or reset process as described above with reference to block 324.

During process 400, if the measured voltage level of the secondary battery 254 is greater than the predetermined passivation minimum voltage threshold and less than the predetermined maximum passivation voltage threshold, then the processor 104 activates one or more peripheral devices to apply at least one discharge pulse to the secondary battery 254 up to a predetermined maximum number of discharge pulses (blocks 428 and 432). The processor 104 activates one or more peripheral devices, such as the wireless transceiver 144, for a predetermined period of time to draw current from the secondary battery 254 to reduce or eliminate the passivation layer within the secondary battery, followed by an idle period to enable the secondary battery 254 to return to a quiescent state. In another configuration, the processor 104 activates a backlight or other power-consuming components in an LCD, OLED or other display device (a user I/O peripheral 140) to apply the discharge pulse instead of or in addition to the operation of the wireless transceiver 144. The process 400 then returns to the processing of block 408 to enable the processor 104 to receive another voltage measurement of the secondary battery 254. The time duration of each discharge pulse and maximum number of discharge pulses for the secondary battery 254 may be different than for the primary battery 228 due to the differences in loads that are connected to each battery. For example, in the medical device 200 the processor 104 is configured to apply a maximum of two discharge pulses to the primary battery 228 in the process 300, while the processor 104 is configured to apply a maximum of three discharge pulses to the secondary battery 254 in the process 400, although the precise maximum number of discharge pulses may vary for other embodiments. The discharge pulses compensate for potential passivation in the secondary battery 254 in a similar manner to the compensation for passivation in the primary battery 228 that is described above in FIG. 3.

During the process 400, the processor 104 performs a loop of the operations described in blocks 408-432 described above until the measured voltage level of the secondary battery 254 either drops to less than or equal to the predetermined passivation minimum voltage threshold (blocks 412 and 418), increases to greater than or equal to the predetermined passivation maximum voltage threshold (blocks 420-424), or the processor 104 reaches the maximum number of discharge pulses without meeting either of the two conditions described above (block 428). After completing the maximum number of discharge pulses, if the measured voltage level of the secondary battery 254 is greater than or equal to the predetermined high battery voltage threshold or the predetermined operating voltage threshold (block 436), then the processor 104 continues with operation of the peripheral device or devices that receive power from the secondary battery 254 (block 424). The processor 104 optionally generates an alert message with an output device 140 to indicate a low battery condition for the secondary battery 254 if the voltage of the secondary battery 254 is greater than or equal to the predetermined operating voltage threshold but remains below the predetermined high battery voltage threshold.

After completion of the maximum number of discharge pulses, if the voltage level of the secondary battery 254 remains below the predetermined operating voltage threshold (block 436), then the processor 104 identifies if the measured voltage for the secondary battery 254 is greater than or equal to the predetermined minimum voltage threshold for the secondary battery 254 (block 440). If the secondary battery voltage is greater than the predetermined minimum voltage threshold then the processor 104 generates the error code indicating that the secondary battery 254 should be replaced (block 416) and ceases operation of the medical device 200 (block 418). The processor 104 also stores the error code for the secondary battery 254 in the error code data 120 of the memory 116. While the medical device 200 does not continue operation, in some configurations the processor 104 generates an output using one or more of the I/O devices 140 to alert the user to the need to replace the secondary batter 254 to enable the medical device 200 to resume operation if the voltage level of the secondary battery 254 is greater than or equal to the minimum voltage threshold. If the voltage level of the secondary battery 254 is less than the predetermined minimum voltage threshold, then the processor 104 immediately ceases operation of the medical device 200 (block 418).

As described above, the process 400 enables the medical device 200 to apply discharge pulses that compensate for potential battery passivation in the secondary battery 254 during a device startup operation. The passivation compensation process enables the medical device 200 to reduce or eliminate false alarm conditions in which the medical device 200 incorrectly alerts a user to a low battery condition of the secondary battery 254 (when the passivation compensation returns battery voltage to ≥predetermined high battery voltage threshold) or to prevent an incorrect battery replacement error that prevents standard operation of the peripheral in the medical device 200 (when the passivation compensation returns battery voltage to 2 predetermined operating voltage threshold).

While the exemplar battery-powered medical device described above is a blood glucose meter, those of skill in the art will recognize that the devices and methods described herein are equally applicable to a wide range of battery-operated medical devices that experience battery passivation. In particular, even medical devices that operate continuously or with a high duty cycle after activation may experience battery passivation during shipment and storage prior to being activated. Examples of such devices include, but are not limited to, pumps that deliver controlled doses of insulin or other pharmaceuticals to a user over time and continuous glucose monitors.

This disclosure is described in connection with what are considered to be the most practical and preferred embodiments. However, these embodiments are presented by way of illustration and is not intended to be limited to the disclosed embodiments. Accordingly, one of skill in the art will realize that this disclosure encompasses all modifications and alternative arrangements within the spirit and scope of the disclosure and as set forth in the following claims.

What is claimed is:

1. A method for operating a medical device comprising:
    activating a processor in the medical device in a low-power operating mode, the processor receiving electrical power from a battery electrically connected to the medical device;
    measuring, with the processor, a first voltage level of the battery;
    applying, with the processor, at least one discharge pulse to the battery in response to the first voltage level of the battery being greater than a predetermined passivation minimum voltage threshold and less than a predetermined passivation maximum voltage threshold;
    measuring, with the processor, a second voltage level of the battery after the at least one discharge pulse; and
    operating the processor in the medical device in an increased-power operating mode to continue operation of the medical device only in response to the second voltage level being greater than or equal to a predetermined operating voltage threshold, the predetermined operating voltage threshold being greater than the predetermined passivation minimum voltage threshold and less than or equal to the predetermined passivation maximum voltage threshold.

2. The method of claim 1 further comprising:
    continuing to operate the processor in the low-power mode to generate an error code that is stored in a memory in response to the second voltage level of the battery being less than the predetermined operating voltage threshold and greater than a predetermined minimum voltage threshold, the predetermined minimum voltage threshold being greater than or equal to the passivation minimum voltage threshold; and
    deactivating, with the processor, the medical device.

3. The method of claim 2 further comprising:
    deactivating, with the processor, the medical device in response to the second voltage level of the battery being less than the predetermined minimum voltage threshold.

4. The method of claim 2 further comprising:
    deactivating, with the processor, the medical device in response to the first voltage level of the battery being less than the predetermined passivation minimum voltage threshold.

5. The method of claim 1, the applying of the at least one discharge pulse further comprising:
    increasing a clock speed of the processor to operate the processor in the increased-power operating mode for a predetermined period of time to draw electrical current from the battery; and
    reducing the clock speed of the processor to operate the processor in the low-power operating mode after the predetermined period of time.

6. The method of claim 1, the applying of the at least one discharge pulse further comprising:
    activating, with the processor, at least one peripheral device in the medical device for a predetermined period of time to draw electrical current from the battery; and
    deactivating, with the processor, the at least one peripheral device after the predetermined period of time.

7. The method of claim 6, wherein the at least one peripheral device is one or more of a wireless data transceiver, a display screen, and an electromechanical actuator.

8. The method of claim 1, wherein the processor measures the second voltage level of the battery after two discharge pulses.

9. The method of claim 1 further comprising:
operating the processor in the medical device in the increased-power operating mode to continue operation of the medical device to generate a blood glucose measurement.

10. A method for operating a medical device comprising:
activating a processor in the medical device in a low-power operating mode, the processor receiving electrical power from a primary battery electrically connected to the medical device;
measuring, with the processor, a first voltage level of the primary battery;
receiving, with the processor, a second voltage level of a secondary battery electrically connected to the medical device that provides electrical power to at least one peripheral device in the medical device;
increasing a clock speed of the processor to apply at least one discharge pulse to the primary battery in response to the first voltage level of the primary battery being greater than a predetermined passivation minimum voltage threshold and less than a predetermined passivation maximum threshold;
activating, with the processor, the at least one peripheral device in the medical device to apply at least one discharge pulse to the secondary battery in response to the second voltage level of the secondary battery being greater than the predetermined passivation minimum voltage threshold and less than the predetermined passivation maximum threshold;
measuring, with the processor, a third voltage level of the primary battery after the at least one discharge pulse applied to the primary battery;
measuring, with the processor, a fourth voltage level of the secondary battery after the at least one discharge pulse applied to the secondary battery; and
operating the processor in the medical device in the increased-power operating mode and activating the at least one peripheral device to continue operation of the medical device only in response to the third voltage level being greater than or equal to a first predetermined operating voltage threshold, the first predetermined operating voltage threshold being greater than the predetermined passivation minimum voltage threshold and less than or equal to the predetermined passivation maximum voltage threshold, and the fourth voltage level being greater than or equal to a second predetermined operating voltage threshold, the second predetermined operating voltage threshold being greater than the predetermined passivation minimum voltage threshold and less than or equal to the predetermined passivation maximum voltage threshold.

11. The method of claim 10 further comprising:
continuing to operate the processor in the low-power mode to generate an error code that is stored in a memory in response to the third voltage level of the primary battery being less than the first predetermined operating voltage threshold and greater than a first predetermined minimum voltage threshold and the fourth voltage level of the secondary battery being less than the second predetermined operating voltage threshold and greater than a second predetermined minimum voltage threshold; and
deactivating, with the processor, the medical device.

12. The method of claim 10, wherein the applying of the at least one discharge pulse to the primary battery occurs prior to the applying of the at least one discharge pulse to the secondary battery.

13. The method of claim 10, wherein the applying of the at least one discharge pulse to the primary battery occurs concurrently to the applying of the at least one discharge pulse to the secondary battery.

14. The method of claim 11, wherein the first predetermined minimum voltage threshold is equal to the second predetermined minimum voltage threshold and the first predetermined operating voltage threshold is equal to the second predetermined operating voltage.

15. The method of claim 10, wherein a power management integrated circuit (PMIC) measures the second voltage level of the secondary battery and provides the second voltage level to the processor.

16. The method of claim 10, wherein the at least one peripheral device is a wireless data transceiver.

17. The method of claim 10 wherein the at least one peripheral device is a display device.

18. The method of claim 10, wherein the processor measures the third voltage level of the primary battery after applying two discharge pulses to the primary battery.

19. The method of claim 10, wherein the processor measures the fourth voltage level of the secondary battery after applying three discharge pulses to the secondary battery.

20. The method of claim 10 further comprising:
operating the processor in the medical device in the increased-power operating mode and activating the at least one peripheral device in the medical device to continue operation of the medical device to generate a blood glucose measurement.

\* \* \* \* \*